US00PP37070P2

(12) United States Plant Patent
Rouwette

(10) Patent No.: US PP37,070 P2
(45) Date of Patent: Oct. 28, 2025

(54) ***HYDRANGEA* PLANT NAMED 'GRHYAR2008'**

(50) Latin Name: *Hydrangea arborescens*
Varietal Denomination: GRHYAR2008

(71) Applicant: Guido Rouwette, Valkenburg (NL)

(72) Inventor: Guido Rouwette, Valkenburg (NL)

( * ) Notice: Subject to any disclaimer, the term of this patent is extended or adjusted under 35 U.S.C. 154(b) by 0 days.

(21) Appl. No.: 19/036,991

(22) Filed: Jan. 24, 2025

(30) Foreign Application Priority Data

Aug. 6, 2024 (QZ) ..... PBR 20241816

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02; A01H 5/00; A01H 6/48
See application file for complete search history.

(56) References Cited

U.S. PATENT DOCUMENTS

PP35,835 P2 * 5/2024 Hara ..... Plt./250

OTHER PUBLICATIONS

Heco Stekcultures B.V. retrieved on Apr. 7, 2025 at https://hecostek.nl/en/voorraad/, 5 pp. (Year: 2025).*
Globe Planter Hortensia Candybelle Winegum retrieved on Apr. 7, 2025 at https://www.globeplanter.com/plante-Hydrangea-Winegum-8828.html, 2 pp. (Year: 2025).*

* cited by examiner

*Primary Examiner* — June Hwu
(74) *Attorney, Agent, or Firm* — Penny J. Aguirre

(57) ABSTRACT

A new cultivar of *Hydrangea arborescens* plant named 'GRHYAR2008' that is characterized by its inflorescences with flowers that are deep purple in color that change to red-purple in color and finally light purple-pink in color, its medium sized and compact plant habit, its large flower panicles, and its sturdy stems.

3 Drawing Sheets

Botanical classification: *Hydrangea arborescens.*
Varietal Denomination: 'GRHYAR2008'.

CROSS-REFERENCE TO A RELATED APPLICATION

This application is related to a European Community Plant Variety Office (CPVO) Plant Breeder's Rights Application No. 2024/1816 filed on Aug. 6, 2024, under 35 U.S.C. 119(f), the entire contents of which is incorporated by reference herein. The Applicant received the information for the Plant breeders' rights application directly from the Inventor.

BACKGROUND OF THE INVENTION

The present invention relates to a new and distinct cultivar of *Hydrangea arborescens* and will be referred to hereafter by its cultivar name, 'GRHYAR2008'. 'GRHYAR2008' represents a new cultivar of smooth *Hydrangea*, a perennial shrub grown for landscape use.

The new *Hydrangea* resulted from a controlled breeding program conducted by the Inventor in Valkenburg, The Netherlands. The goals of the breeding program were to develop new cultivars of *Hydrangea arborescens* with sturdy stems, healthy foliage, medium and compact plant sizes, large panicles, and unique flower panicle colors. The Inventor made crosses in July 2017 between unnamed and unpatented proprietary plants of *Hydrangea arborescens* in the Inventor's breeding program as both the female and male parents. 'GRHYAR2008' was selected as a single unique plant in July of 2020 from the resulting seedlings of the above crosses.

Asexual propagation of the new cultivar was first accomplished by stem cuttings by the Inventor in summer of 2018 in Valkenburg, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'GRHYAR2008' as a unique cultivar of *Hydrangea.*

1. 'GRHYAR2008' exhibits inflorescences with flowers that are red-purple in color and change to light purple-pink in color.
2. 'GRHYAR2008' exhibits a medium sized, compact plant habit.
3. 'GRHYAR2008' exhibits large flower panicles.
4. 'GRHYAR2008' exhibits sturdy stems.

Both of the parents of 'GRHYAR2008' have inflorescences with sterile flower sepals that are rosy-pink in color. 'GRHYAR2008' can be most closely compared to the *Hydrangea arborescens* cultivars 'GRHYAR1407' (U.S. Plant Pat. No. 31,016) and 'Hyso22' (U.S. Plant Pat. No. 35,835). 'GRHYAR1407' is similar to 'GRHYAR2008' in having a medium plant size, a compact plant habit, and sturdy stems. differs from 'GRHYAR2008' in having sterile flower sepals that are light pink without any violet-purple tones in color. 'Hyso22' is similar to 'GRHYAR2008' in having a medium plant size and a compact plant habit. 'Hyso22' differs from 'GRHYAR2008' in having sterile flower sepals that are more pink in color with greenish white undertones as they age.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Vitaflora, Lendert de Vos, florapedia, Green & Future Farm notice, Golden Plants, Hekostek, and Campus Rings.

BRIEF DESCRIPTION OF THE DRAWINGS

The accompanying color photographs illustrate the overall appearance and distinct characteristics of the new *Hydrangea*. The photographs were taken of a three-year-old plants as grown outdoors in a trial garden in Walkenburg, The Netherlands.

The photograph in FIG. 1 provides a side view of the plant habit of 'GRHYAR2008' in bloom.

Figure 1:
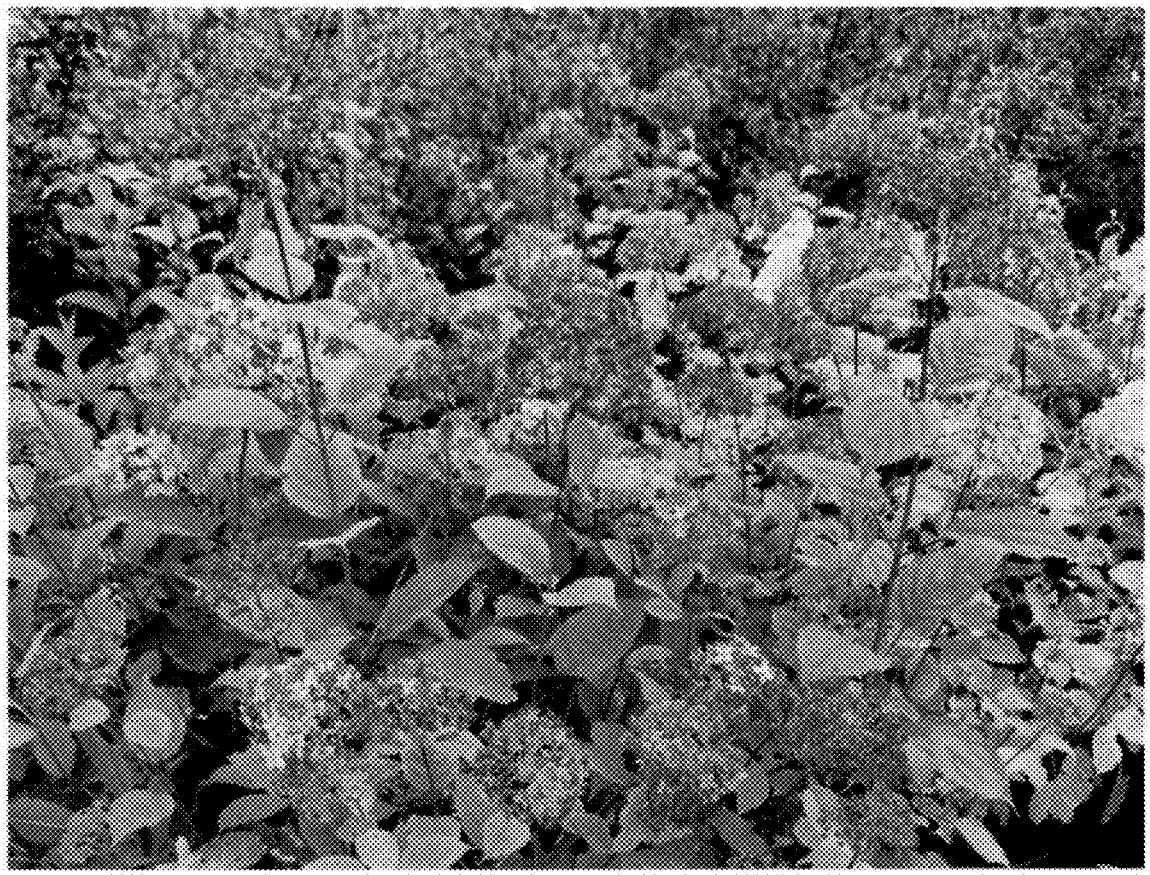
Figure 2:
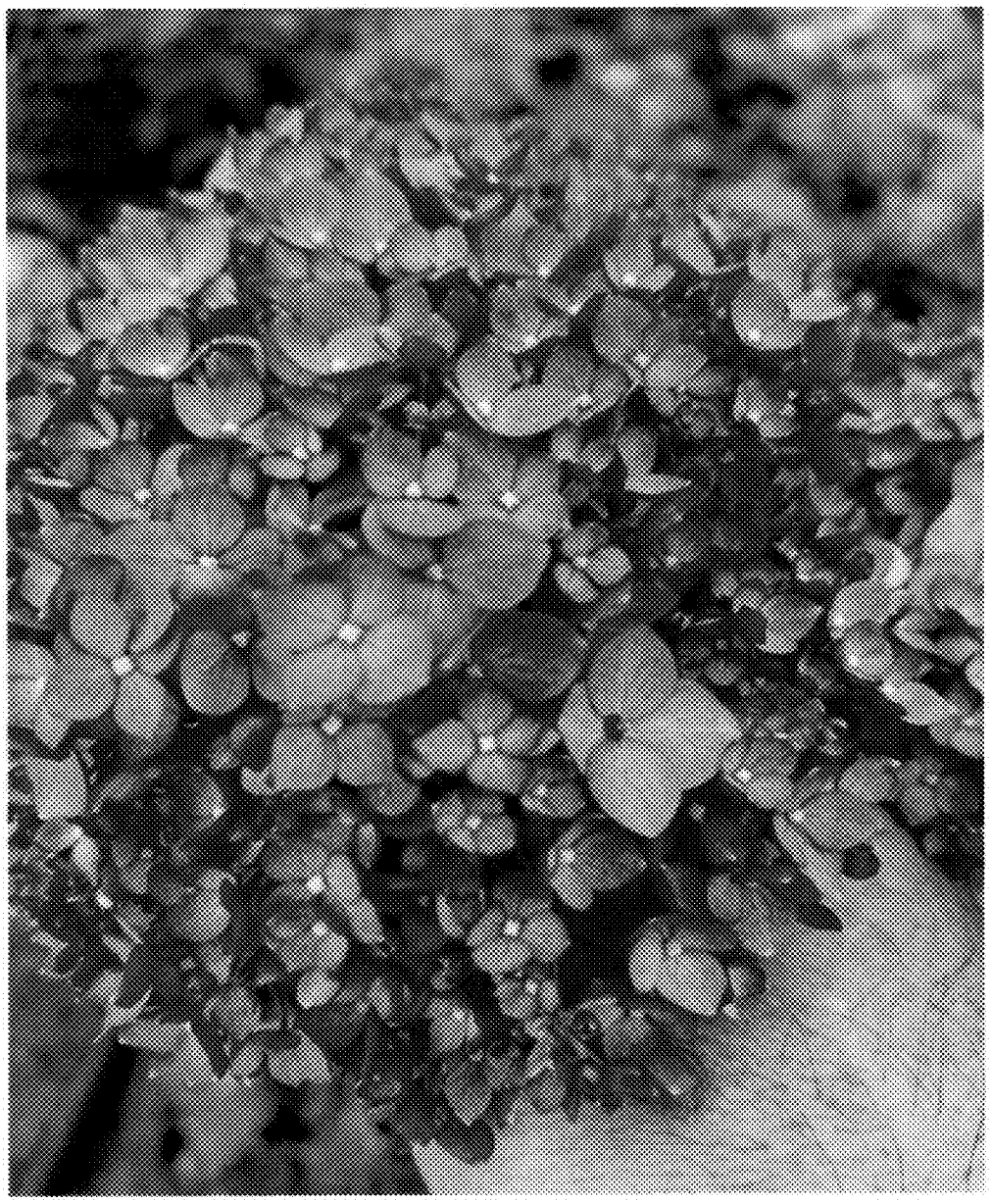

The photograph in FIG. 2 provides a close-up view of an inflorescence of 'GRHYAR2008'.

Figure 3:
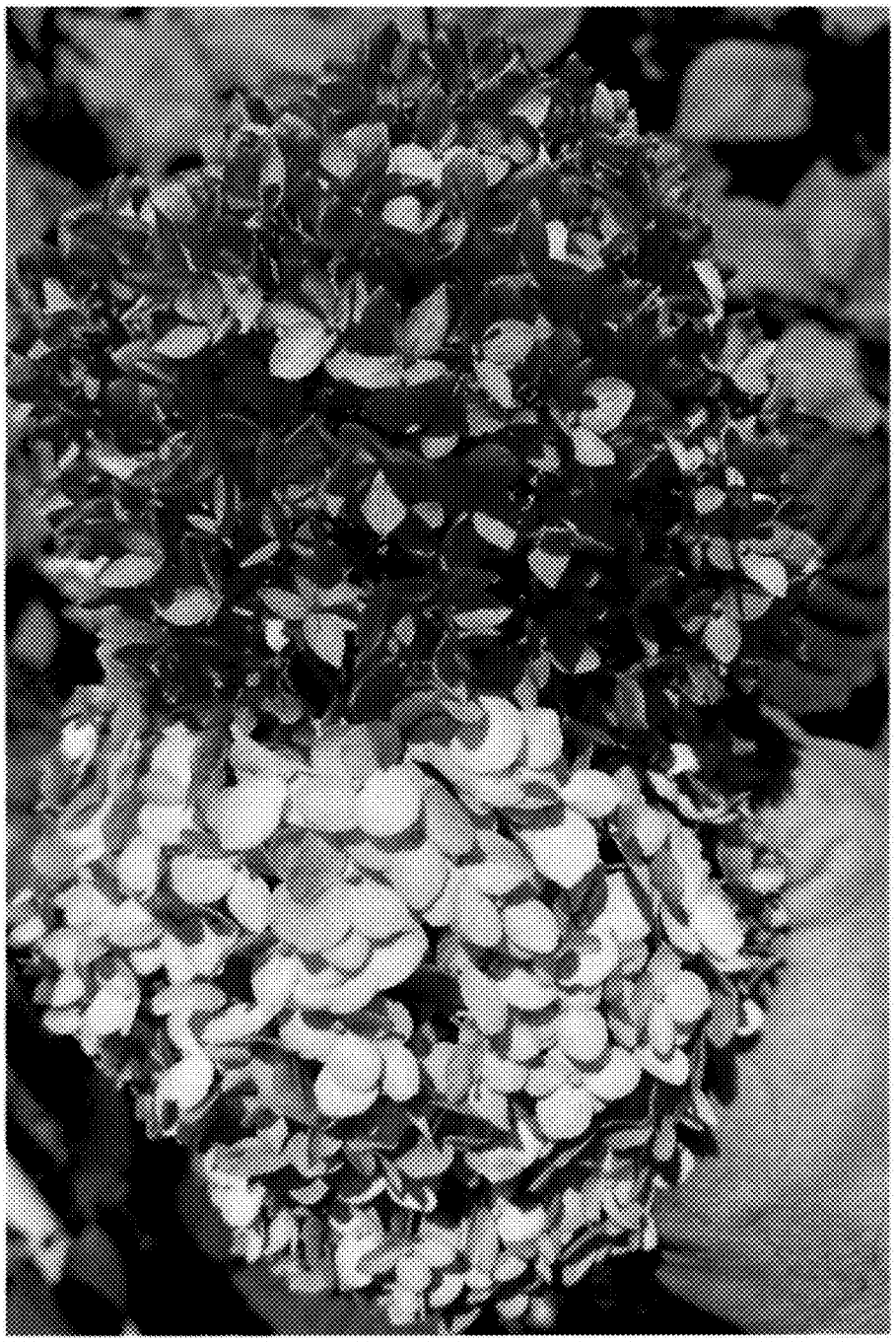

The photograph in FIG. 3 provides a comparison of an inflorescence of 'GRHYAR2008' (top) and an inflorescence of 'GRHYAR1407' (below).

The colors in the photographs are as close as possible with the photographic and printing technology utilized and the color values cited in the detailed botanical description accurately describe the colors of the new *Hydrangea.*

BOTANICAL DESCRIPTION OF THE PLANT

The following is a detailed description of three-year-old plants of 'GRHYAR2008' as grown outdoors in 21-cm containers in Waddinxveen, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—July through September in The Netherlands.

*Plant type.*—Deciduous shrub, mop-head type *Hydrangea.*

*Plant habit.*—Upright and compact.

*Height and spread.*—Reaches 74 cm in height and 68 cm in spread as a 3-year-old plant as grown in a container, reaches 80 to 100 cm in height and 80 cm in spread as grown in the landscape.

*Hardiness.*—At least in U.S.D.A. Zones 4 to 9.

*Diseases and pests.*—No susceptibility and resistance to diseases or pests has been observed.

*Root description.*—Fine, fibrous and dense, NN155A and 164A in color.

*Propagation.*—Stem cuttings.

*Root development.*—6 to 8 weeks for root initiation with a finished plant produced in in a P9 container in about 12 months from a rooted cutting.

*Growth rate and vigor.*—Vigorous.

Stem description:

*Stem shape.*—Rounded.

*Stem strength.*—Strong.

*Stem color.*—Young; 144A to 144B, lightly flushed with 183A to 183B, mature and older wood; N199B and 200C.

*Stem size.*—Average of 50 cm in length (excluding inflorescence) and 5 mm in diameter.

*Stem surface.*—Glabrous.

*Stem aspect.*—Upright to slightly outward.

*Branching.*—Freely branching with an average of 12 lateral branches.

Foliage description:

*Leaf shape.*—Broadly ovate.

*Leaf arrangement.*—Opposite.

*Leaf division.*—Simple.

*Leaf base.*—Rounded to cordate.

*Leaf apex.*—Slightly acuminate.

*Leaf margins.*—Serrate.

*Leaf venation.*—Pinnate, color; matches leaf surfaces.

*Leaf size.*—An average of 12 cm in length and 10 cm in width.

*Leaf attachment.*—Petiolate.

*Leaf number.*—An average of 10 per lateral stem.

*Leaf surface.*—Both surfaces slightly pubescent.

*Leaf color.*—Young upper surface; 144C, young lower surface; 145C to 145D, mature upper surface; 144A, mature lower surface; 138A.

*Petioles.*—An average of 3 cm in length, 2 mm in diameter, surface is slightly pubescent, color; upper and lower side 144A to 144B.

Inflorescence description:

*Inflorescence type.*—Terminal mop-head panicle, comprised of sterile flowers above inconspicuous fertile flowers, broadly conical in shape.

*Lastingness of inflorescence.*—Sterile flowers; persistent for an average of 6 weeks, fertile flowers; self-cleaning, an average of 5 days.

*Inflorescence number.*—One per lateral stem.

*Inflorescence size.*—An average of 9 cm in height and 16 cm in diameter.

*Flower number.*—An average of 300 sterile flowers and 150 fertile flowers per panicle.

*Flower fragrance.*—None.

*Flower aspect.*—Sterile flowers; held upright to outward and slightly drooping, fertile flowers; held upright from peduncle.

*Flower size.*—Sterile flowers; 1.7 cm in diameter and 0.7 mm in depth, fertile flowers; an average of 6 mm in diameter and 5 mm in depth.

*Flower type.*—Sterile flowers rotate, fertile flowers rotate and dropped when mature.

*Flower buds.*—Sterile flowers; an average of 2 mm in length and diameter, ovate in shape, 157C in color with a hint of 59D, fertile flowers; an average of 2 mm in length and diameter, ovate in shape, 157C in color with a hint of 59D.

*Petals*.—Sterile flowers; 4, not opening, remaining in bud-stage; length of petal 2 mm, glabrous, matte surfaces, fertile flowers; 5, rotate in shape, ovate in shape, acute apex, truncate base, entire margins, average of 1.5 mm in length and width, both surface glabrous, color; when opening and fully open upper and lower surface 157C, petals drop at maturity.

*Peduncles*.—Up to 65 cm in length, 5 mm in width, color; 144A to 144B, flushed with 183A.

*Pedicels*.—Sterile flowers; moderate strength, an average of 8 mm in length and 1 mm in width, 145C in color, surface is slightly pubescent, fertile flowers; moderate strength, an average of 3 mm in length, 1 mm in diameter, 145C in color, surface is slightly pubescent.

*Sepals*.—Sterile flowers; 4 to 5, 7 mm in length, 6 mm in width, elliptical to ovate in shape, acute apex, obtuse base, entire margins, overlapping is weak to medium, surfaces are glabrous, color; young upper surface 71B and 70B, margins 71A, young lower surface 71A and 70B, mature upper surface; 70A and 70B, lightly flushed with 71B and 70C, then changing to 69C, margins 71B, mature lower surface; margins 71A to 71B, with a blend of 71B and 70B to 70C, then changing to 71B flushed with 70B and 70C and then to 70D with 69A and margins 71B.

*Bracts*.—None present.

Reproductive organs:

*Gynoecium*.—Sterile flowers; none observed, fertile flowers; 2 pistils, an average of 1 mm in length, stigma; round in shape, NN155D in color, style; 1 mm in length, 145D in color, ovary is 147D in color, 1 mm in diameter.

*Androecium*.—Sterile flowers; none observed, fertile flowers; stamens; average of 9, filaments; 3 mm in length, NN155D in color, anthers; round in shape, 0.5 mm in length, NN155D in color, pollen; none observed.

*Fruit and seed*.—None observed to date.

It is claimed:

1. A new and distinct cultivar of *Hydrangea* plant named 'GRHYAR2008' substantially as herein illustrated and described.

* * * * *